(12) United States Patent
Altamura

(10) Patent No.: US 11,659,985 B2
(45) Date of Patent: *May 30, 2023

(54) UNIVERSAL VAGINAL SPECULUM

(71) Applicant: Michael Altamura, Croton-on-Hudson, NY (US)

(72) Inventor: Michael Altamura, Croton-on-Hudson, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 17/932,476

(22) Filed: Sep. 15, 2022

(65) Prior Publication Data

US 2023/0012080 A1 Jan. 12, 2023

Related U.S. Application Data

(63) Continuation of application No. 16/795,643, filed on Feb. 20, 2020, now Pat. No. 11,464,404, which is a continuation-in-part of application No. 16/395,756, filed on Apr. 26, 2019, now Pat. No. 11,147,445.

(60) Provisional application No. 62/936,738, filed on Nov. 18, 2019.

(51) Int. Cl.
*A61B 1/303* (2006.01)
*A61B 17/42* (2006.01)
*A61B 1/32* (2006.01)

(52) U.S. Cl.
CPC ............... *A61B 1/303* (2013.01); *A61B 1/32* (2013.01); *A61B 17/42* (2013.01)

(58) Field of Classification Search
CPC .......... A61B 1/303; A61B 1/32; A61B 17/42; A61B 17/4241; A61B 1/31
See application file for complete search history.

(56) References Cited

U.S. PATENT DOCUMENTS

| | | | |
|---|---|---|---|
| 3,890,961 A | 6/1975 | Moore et al. | |
| 5,465,709 A | 11/1995 | Dickie et al. | |
| 5,545,122 A * | 8/1996 | Spruill | A61B 1/32 |
| | | | 604/99.04 |
| D403,066 S | 12/1998 | DeFonzo | |
| 5,868,668 A | 2/1999 | Weiss | |
| D417,276 S | 11/1999 | DeFonzo | |
| 6,024,696 A | 2/2000 | Hoftman et al. | |
| 6,468,232 B1 | 10/2002 | Ashton-Miller et al. | |
| 7,070,561 B1 * | 7/2006 | Ansari | A61B 17/42 |
| | | | 600/220 |
| 8,197,402 B1 | 6/2012 | Cedeno | |

(Continued)

OTHER PUBLICATIONS

U.S. Appl. No. 62/668,970, filed May 9, 2018; first named inventor: Michael Altamura; Title: Universal Surgical Vaginal Speculum.

(Continued)

*Primary Examiner* — Kevin T Truong
*Assistant Examiner* — Diana Jones
(74) *Attorney, Agent, or Firm* — Rothwell, Figg, Ernst & Manbeck, P.C.

(57) ABSTRACT

A vaginal speculum that includes a fixed blade and a movable blade. The movable blade designed to be extended or retracted as required in order to adjust to the length of the vaginal canal of the patient undergoing surgery. A vaginal speculum is further designed with a blade angle mechanism and a blade pivoting mechanism that allows and controls the angle and rotation of the blades in relation to its base. Vacuum connection and a light can also be provided.

22 Claims, 22 Drawing Sheets

(56) References Cited

U.S. PATENT DOCUMENTS

| | | | |
|---|---|---|---|
| 8,864,660 B1* | 10/2014 | Yufa | A61B 17/02 |
| | | | 600/219 |
| D726,909 S | 4/2015 | Bennett | |
| 9,179,891 B2 | 11/2015 | Sasady | |
| 10,512,519 B2 | 12/2019 | Swift et al. | |
| D876,624 S | 2/2020 | Theobald et al. | |
| 2002/0055670 A1 | 5/2002 | Weiss | |
| 2003/0225313 A1* | 12/2003 | Borodulin | A61B 1/303 |
| | | | 600/220 |
| 2005/0080320 A1 | 4/2005 | Lee et al. | |
| 2008/0004497 A1* | 1/2008 | Whitehead | A61B 1/0653 |
| | | | 600/184 |
| 2009/0099422 A1 | 4/2009 | George | |
| 2009/0203968 A1* | 8/2009 | Winslow | A61B 1/32 |
| | | | 600/220 |
| 2009/0312610 A1* | 12/2009 | Buchok | A61B 1/00137 |
| | | | 600/223 |
| 2011/0160540 A1* | 6/2011 | Smith | A61B 1/32 |
| | | | 600/222 |
| 2012/0035638 A1* | 2/2012 | Mathaneswaran | A61B 1/32 |
| | | | 248/316.1 |
| 2012/0174675 A1* | 7/2012 | Sasady | A61B 8/4209 |
| | | | 73/632 |
| 2015/0238070 A1* | 8/2015 | Lia | A61B 1/00034 |
| | | | 600/249 |
| 2016/0029882 A1* | 2/2016 | Young | A61B 1/00066 |
| | | | 600/222 |
| 2017/0189004 A1* | 7/2017 | Swift | A61B 17/02 |
| 2018/0132896 A1* | 5/2018 | Begg | A61B 1/32 |
| 2019/0343379 A1 | 11/2019 | Altamura | |
| 2021/0145270 A1 | 5/2021 | Altamura | |

OTHER PUBLICATIONS

Utility U.S. Appl. No. 16/395,756, filed Apr. 26, 2019; first named inventor: Michael Altamura; Title: Universal Surgical Vaginal Speculum.

* cited by examiner

UNIVERSAL VAGINAL SPECULUM

CROSS-REFERENCE TO RELATED APPLICATIONS

The present application is a continuation of U.S. patent application Ser. No. 16/795,643, filed Feb. 20, 2020, which claims priority to U.S. Provisional Patent Application No. 62/936,738, filed Nov. 18, 2019, and is a continuation-in-part of U.S. patent application Ser. No. 16/395,756, filed Apr. 26, 2019, now U.S. Pat. No. 11,147,445, each of which are incorporated herein by reference in their entireties.

BACKGROUND

Surgical vaginal speculums are self-retaining retractors used to obtain exposure to the vaginal canal to permit vaginal surgery. The existing speculums are composed of a blade that is inserted into the vaginal canal and a stem or handle which may or may not incorporate a weight to cause depression of the posterior vaginal wall to create space. The length of the blade for each speculum is fixed for which reason the operating room has to have an array of speculums of different sizes to adjust for the depth of the vagina and, in some cases, none of the array is properly sized for patient's vagina. Furthermore, the existing speculums have a fixed angle between the blade and the stem and, therefore, they are not always a proper fit corresponding to the pitch of the vagina, which depends on the pliability of the posterior wall. This can affect the degree of exposure created by the speculum. Because the pitch of the vagina depends on the pliability of the posterior vaginal wall, the angled speculums, which are meant to be self-retaining, cannot be properly inserted in those cases where the vaginal canal has little or no pliability. In this case, a 90 degree angle speculum is used which requires an assistant to apply downward pressure on the blade since these speculums do not incorporate a weight. And with the existing specula, there is no possibility of rotating the blade to allow for exposure of different parts of the vagina.

SUMMARY

The device and method presented addresses these deficiencies of the current vaginal speculums. As shown on FIGS. 1 and 12 the disclosed universal vaginal speculum includes a fixed blade (2) and a movable blade (1). The movable blade (1) can be extended or retracted as required in order to adjust to the length of the vaginal canal of the patient undergoing surgery. The disclosed vaginal speculum also includes a mechanism to allow the height of the blades above the base to be adjusted. The disclosed vaginal speculum further includes various features and embodiments including a blade angle mechanism and a blade pivoting mechanism, which allows and controls the angle and rotation of the blades in relation to its base. A vacuum connection and a light features are also disclosed.

PARTS LIST

Figure 1:
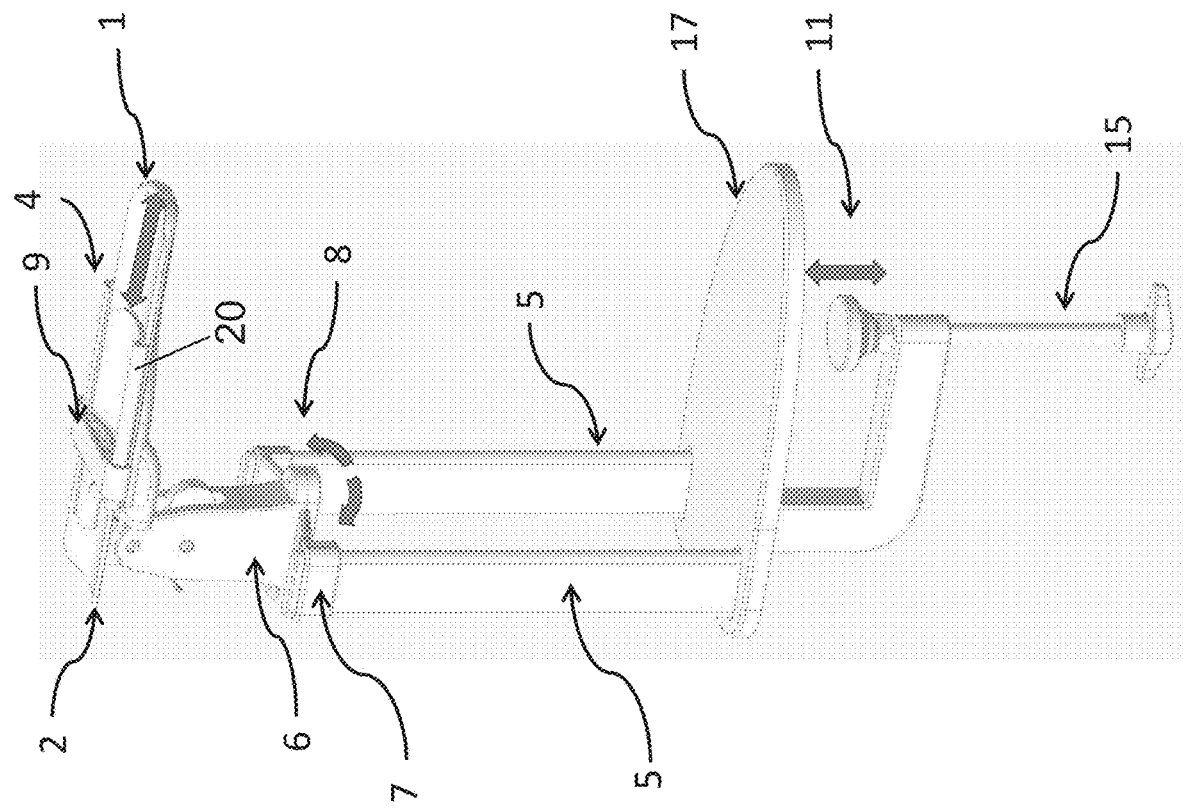
FIG. 1. Shows an isometric view of an exemplary Universal Speculum wherein the blade is extended and at the top most position on the columns.

1. Movable vacuum blade
2. Fixed blade
3. Blade Angle Mechanism
4. Blade Assembly
5. Columns
6. Support Structure
7. Slider track
8. Blade Pivoting Mechanism
9. Light assembly
10. Slider Arm
11. Clamping base assembly
12. Blade vacuum opening
13. Vacuum Connection
14. Pivot Connection
15. Lower Portion of Base Assembly
16. Pivot track
17. Base
20. Rails

DETAILED DESCRIPTION

The Universal Vaginal Speculum disclosed addresses all the above-identified deficiencies of the current vaginal speculums. It adds additional features relative to those included in U.S. patent application Ser. No. 16,395,756, which is incorporated into this disclosure.

The disclosed speculum shown on the figures include a blade assembly (4) with which can be extended or retracted by virtue as warranted for a particular patient. The blade assembly includes a support structure (6) along with a movable suction blade (1), which glides over a fixed blade (2) in order to adjust to the length of the vaginal canal of the patient undergoing surgery. The movable blade (1) can also include an internal cavity with small openings (12) near the front edge and a vacuum connection (13) on the rear of the movable blade (1) to connect to standard medical vacuum tubing, which provides suction to remove surgical and bodily fluids present during operation.

The blade assembly is mounted on at least one column (5) which is mounted a clamping base assembly (11). FIGS. 1-11 depict two columns (5) and FIGS. 12-22 depict one columns (5). The base assembly (11 includes a base (17) in an upper portion of the base assemble which can be designed to slide between the top of the surgical table and the foam table pad. The lower portion of the base assembly (15) can include a clamping mechanism to secure the Universal Vaginal Speculum to a surgical table. The support structure (6) of the blades assembly (4) can further include slides (7) for mounting on the one or more columns (5) to which allows it to be positioned at any height along the height of the column(s) (5).

The Universal Vaginal Speculum can include a blade angle mechanism (3) to allow changing the angle of the blade assembly (4) in an upward or downward direction. One option for the blade angle mechanism (3), which is depicted on the figures, is a spring loaded ratcheting mechanism that allows the angle of the blade assembly (4) to be adjusted so that it corresponds to the vaginal pitch and thereby gain as much exposure as possible depicted on the figures. Other well-known mechanisms to adjust an angle can also be used.

Another feature depicted on the figures is a blade pivoting mechanism (8) to allow the blade assembly (4) to be rotated in a clockwise or counterclockwise direction. This provides improved access to the side walls of the vaginal canal.

FIGS. 1-11 depict one embodiment the pivoting mechanism (8) includes a pivot track (16) on which the blade assembly (4) support structure (6) slides to allow pivoting of the blades.

FIGS. 12-22 depict another embodiment the pivoting mechanism (8) in which the blade assembly includes a pivot connection (14) which allows the blade assembly (4) to pivot 360 degrees.

Figure 2:
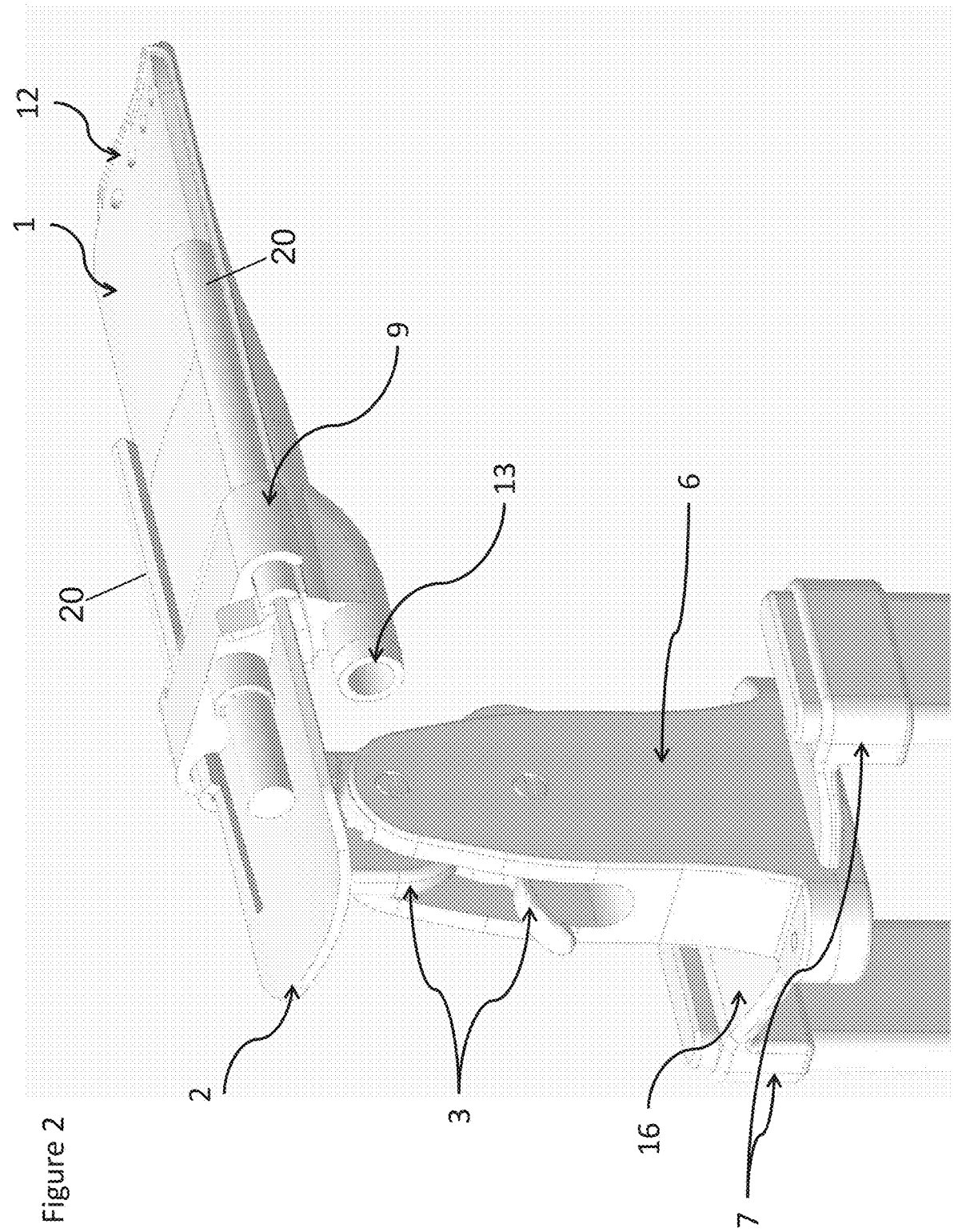
FIG. 2. Shows a close-up isometric view of an exemplary Universal Speculum wherein the blade is extended and the ratchet back side in view.
Figure 3:
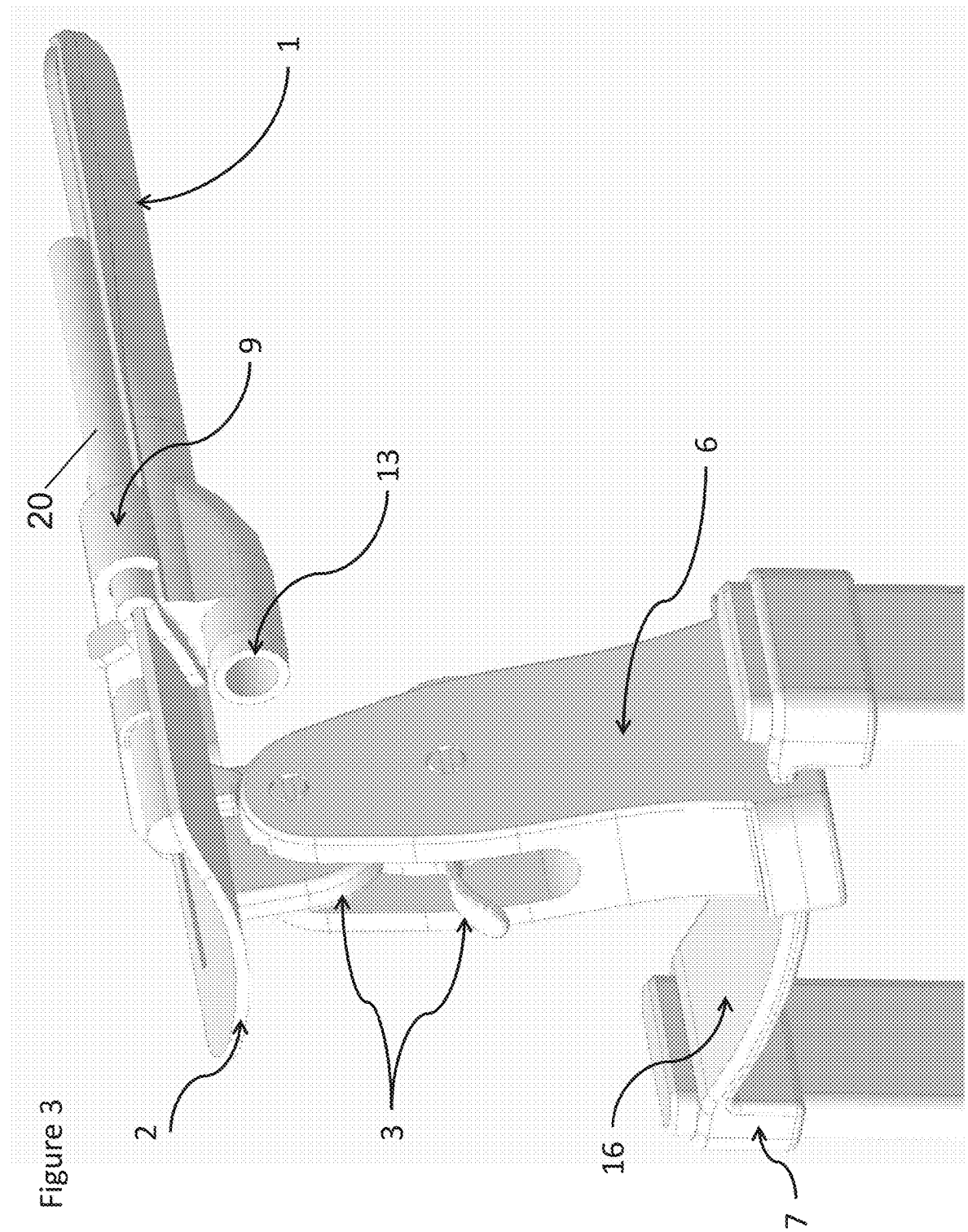
FIG. 3. Shows a close-up isometric view of an exemplary Universal Speculum wherein the blade is extended, the ratchet back side in view, and the blade assembly is pivoted.
Figure 4:
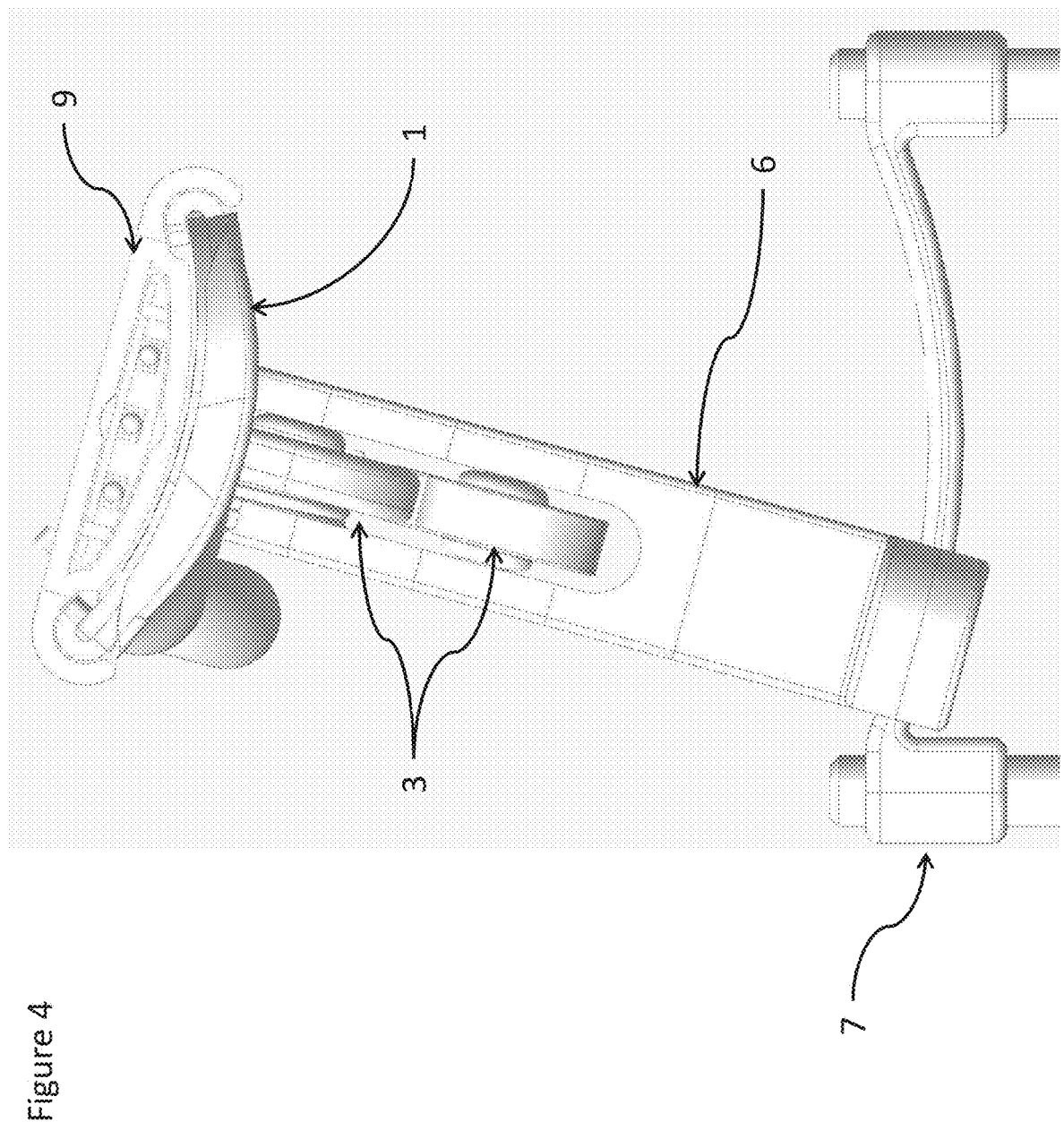
FIG. 4. Shows a close-up front view of an exemplary Universal Speculum wherein the blade is at the top most position on the columns and the blade assembly is pivoted.
Figure 5:
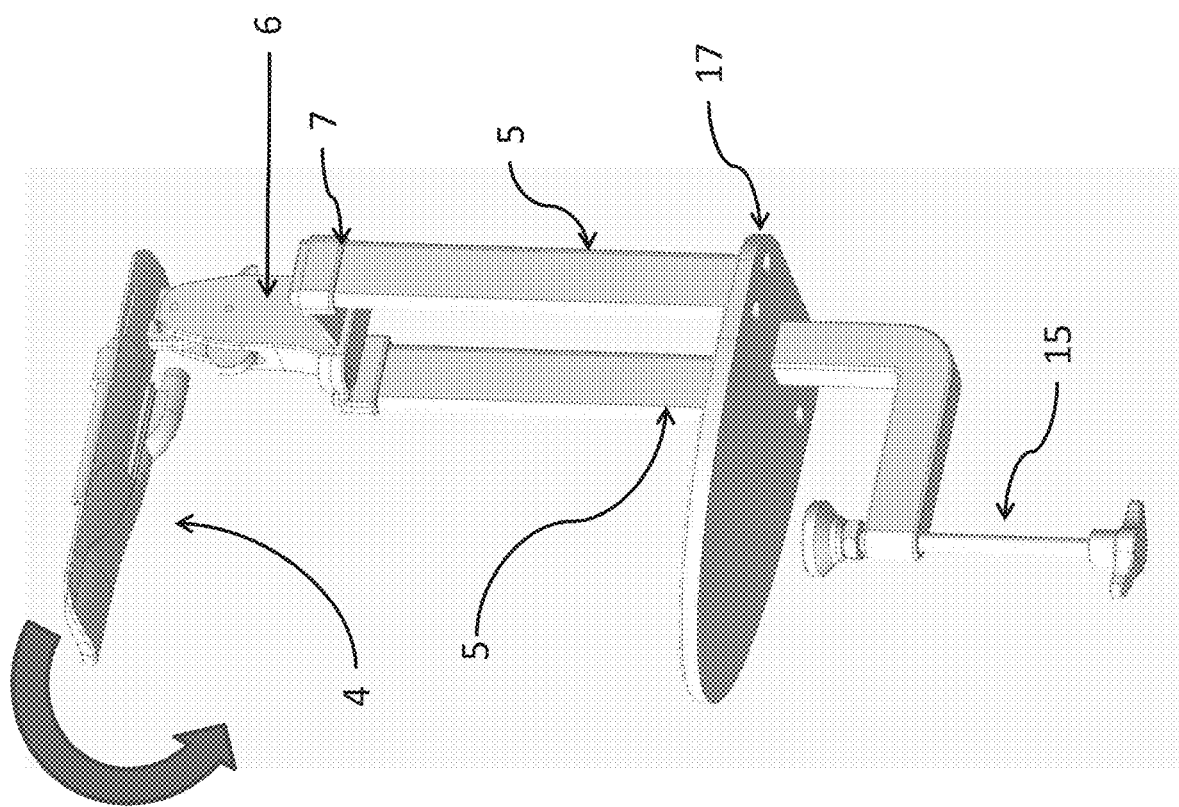
FIG. 5. Shows an isometric view of an exemplary Universal Speculum looking from the bottom up wherein the blade is extended and at the top most position on the columns indicating the rotational angel of the blade motion.
Figure 6:
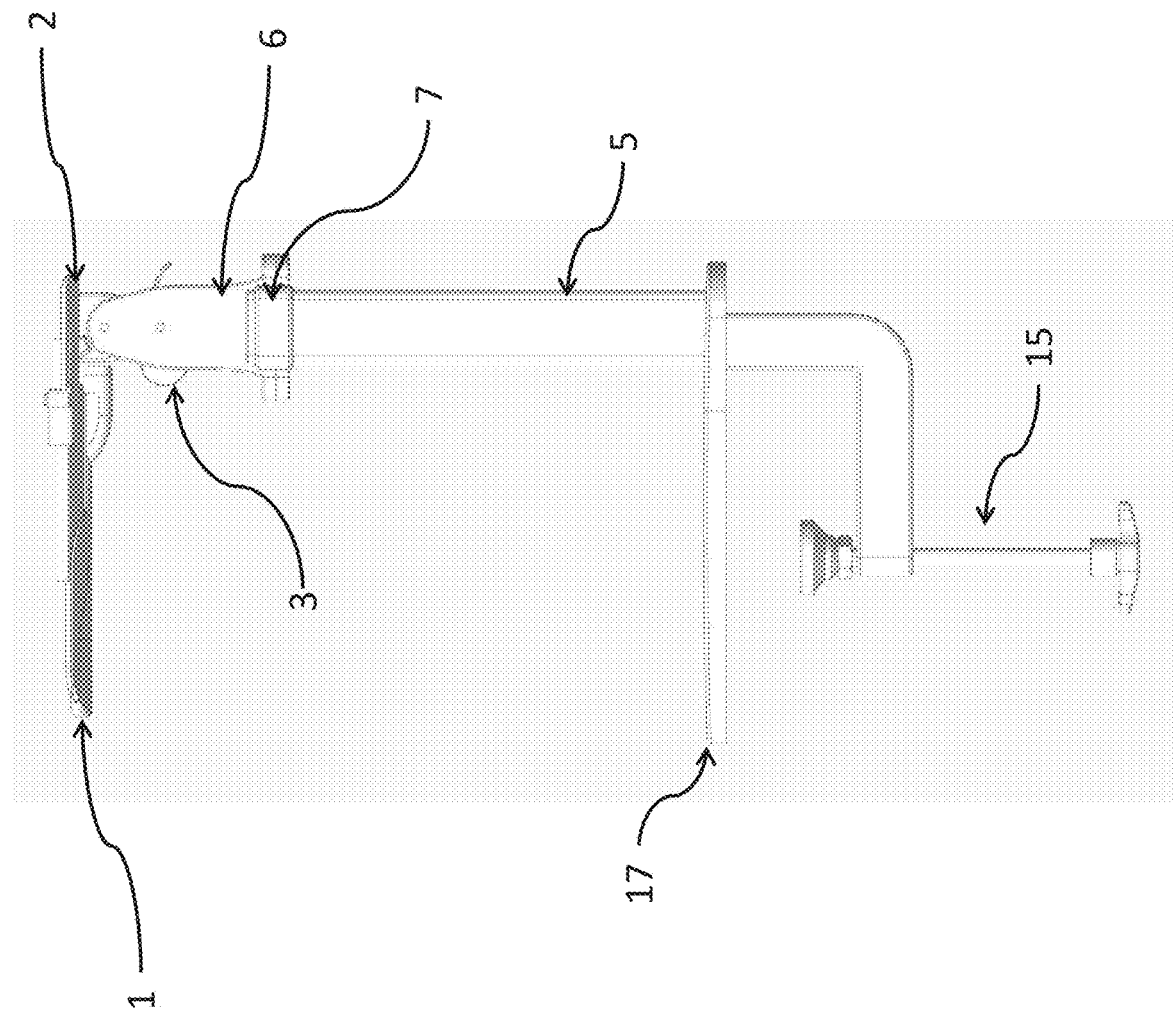
FIG. 6. Shows a side view of an exemplary Universal Speculum wherein the blade is extended and at the top most position on the columns.
Figure 7:
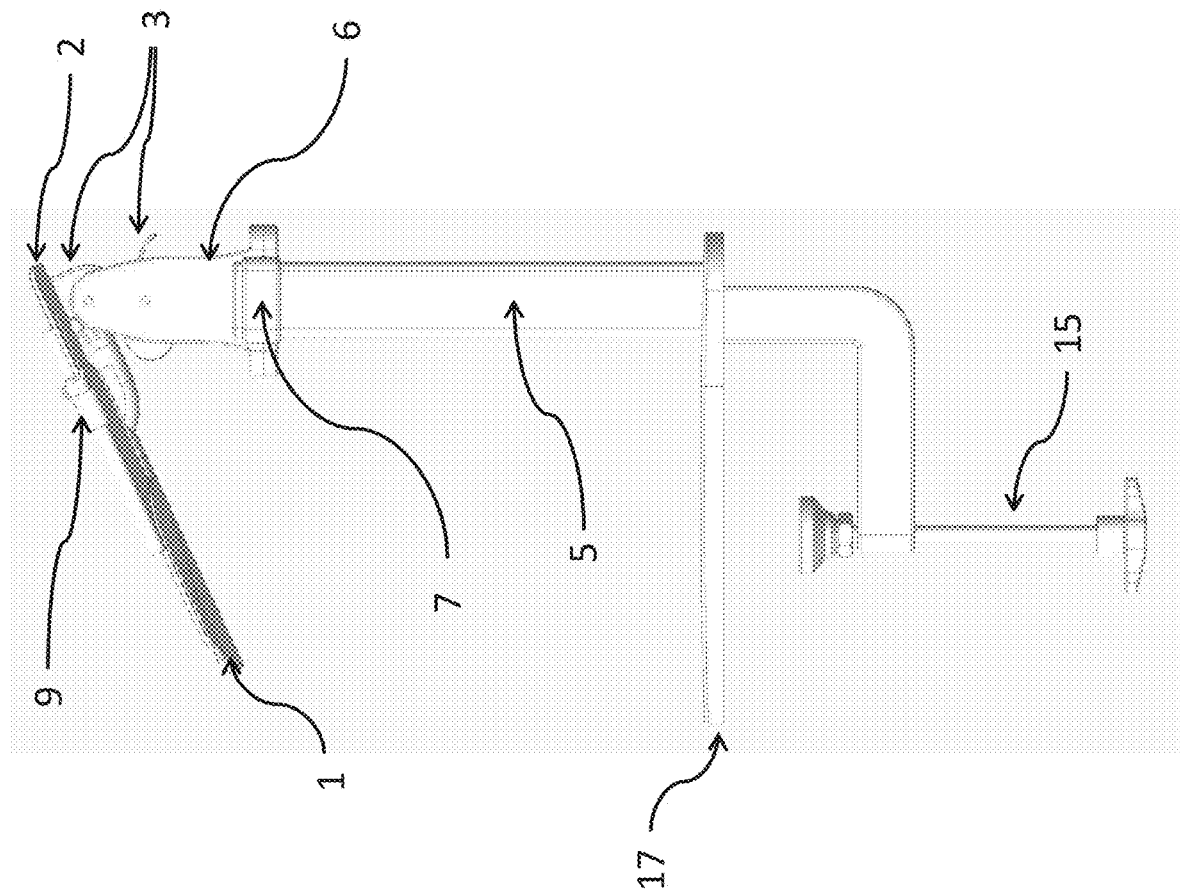
FIG. 7. Shows a side view of an exemplary Universal Speculum wherein the blade is extended, on an angle, and at the top most position on the columns.
Figure 8:
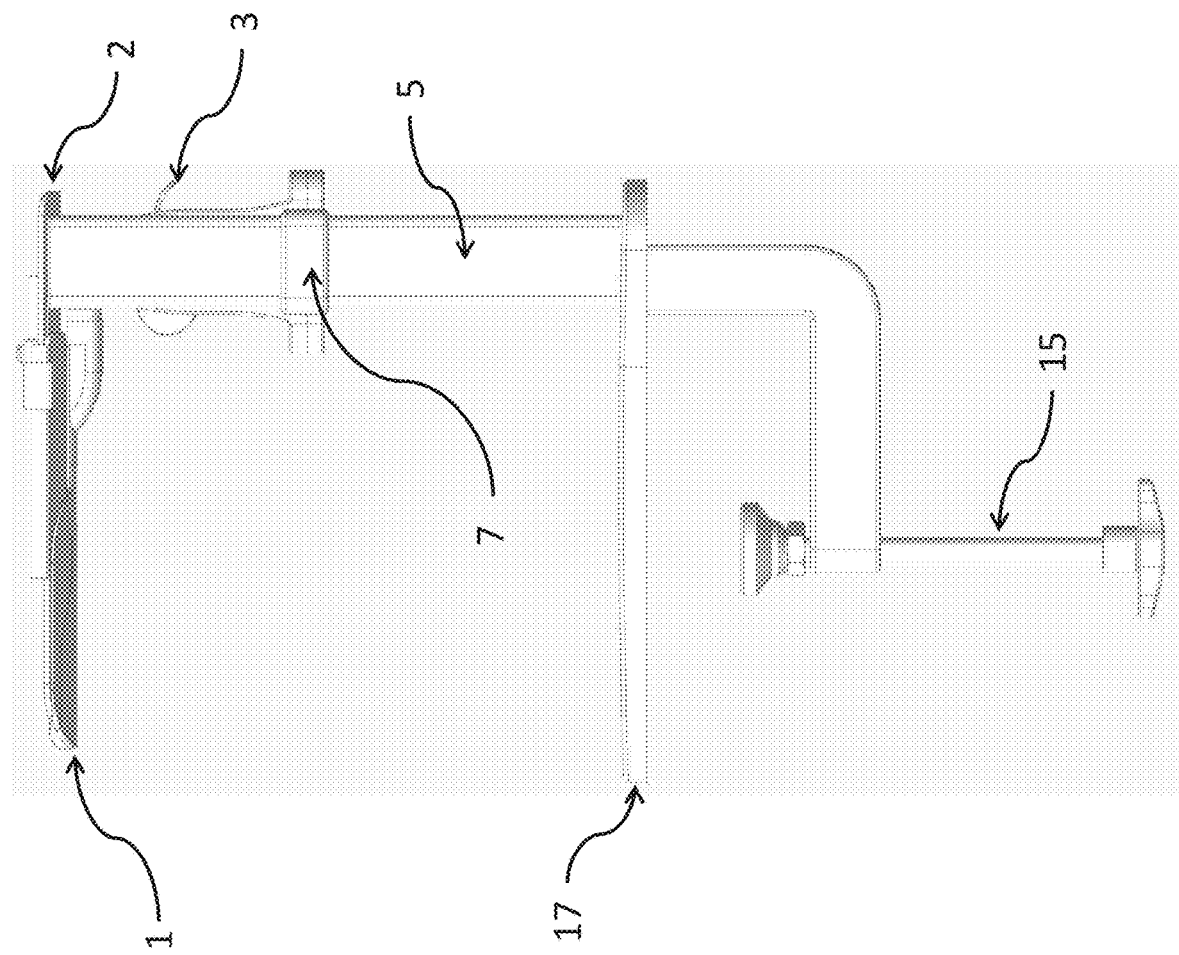
FIG. 8. Shows a side view of an exemplary Universal Speculum wherein the blade is extended and at the bottom most position on the columns.
Figure 9:
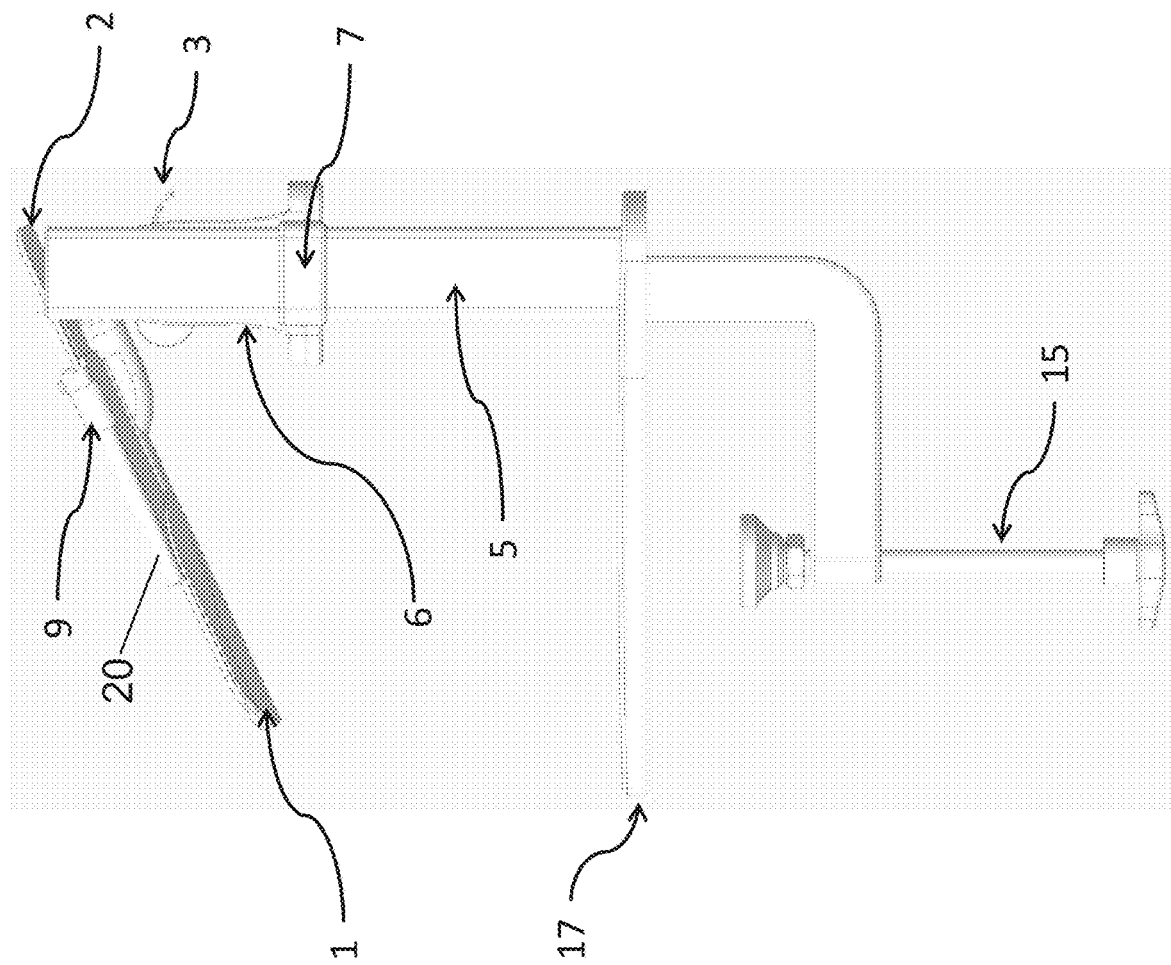
FIG. 9. Shows a side view of an exemplary Universal Speculum wherein the blade is retracted, on an angle, and at the bottom most position on the columns.
Figure 14:
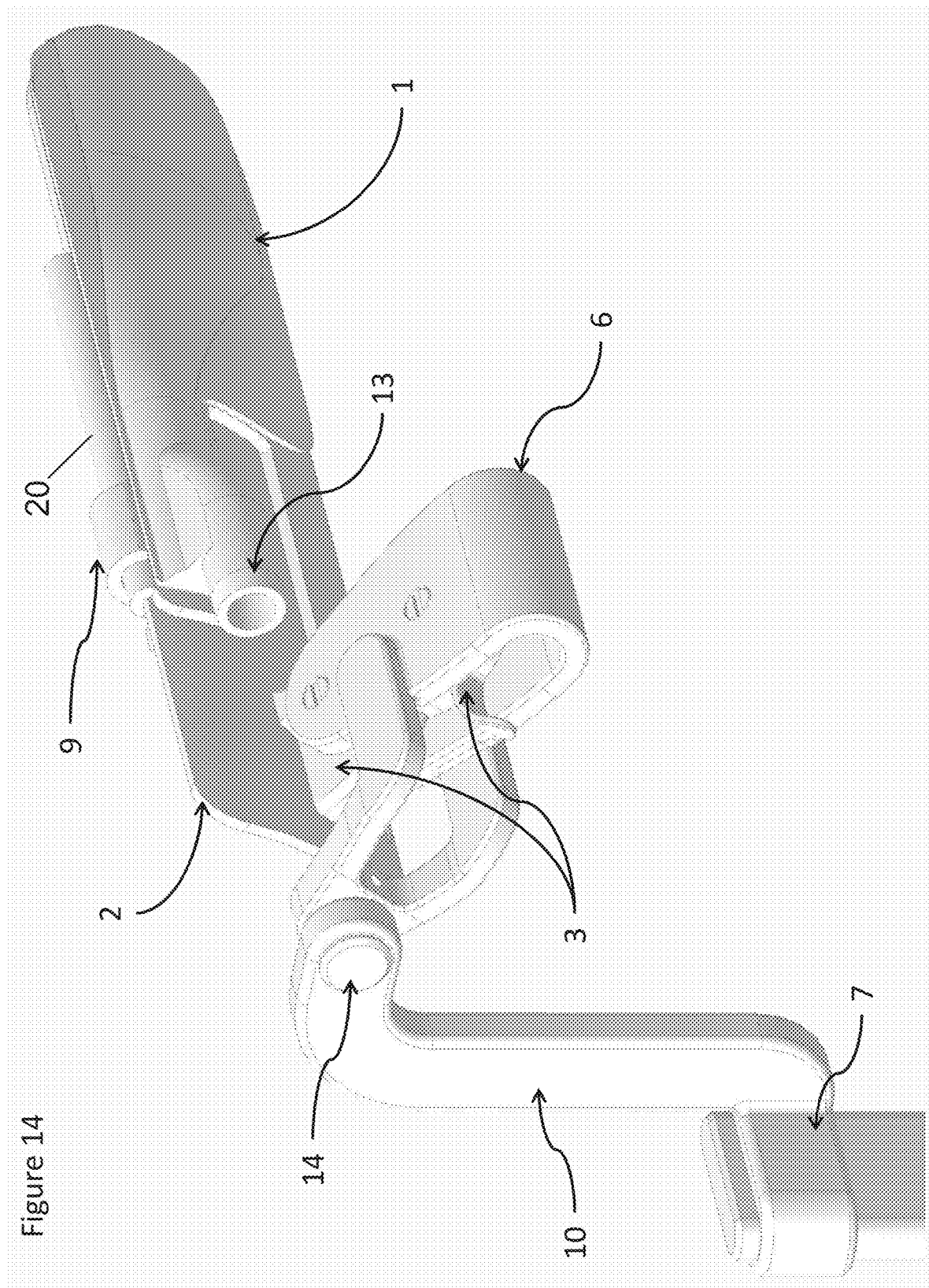
FIG. 14. Shows a close-up isometric view of another embodiment of an exemplary Universal Speculum wherein the blade is extended, the ratchet back side in view, and the blade assembly is pivoted.
Figure 15:
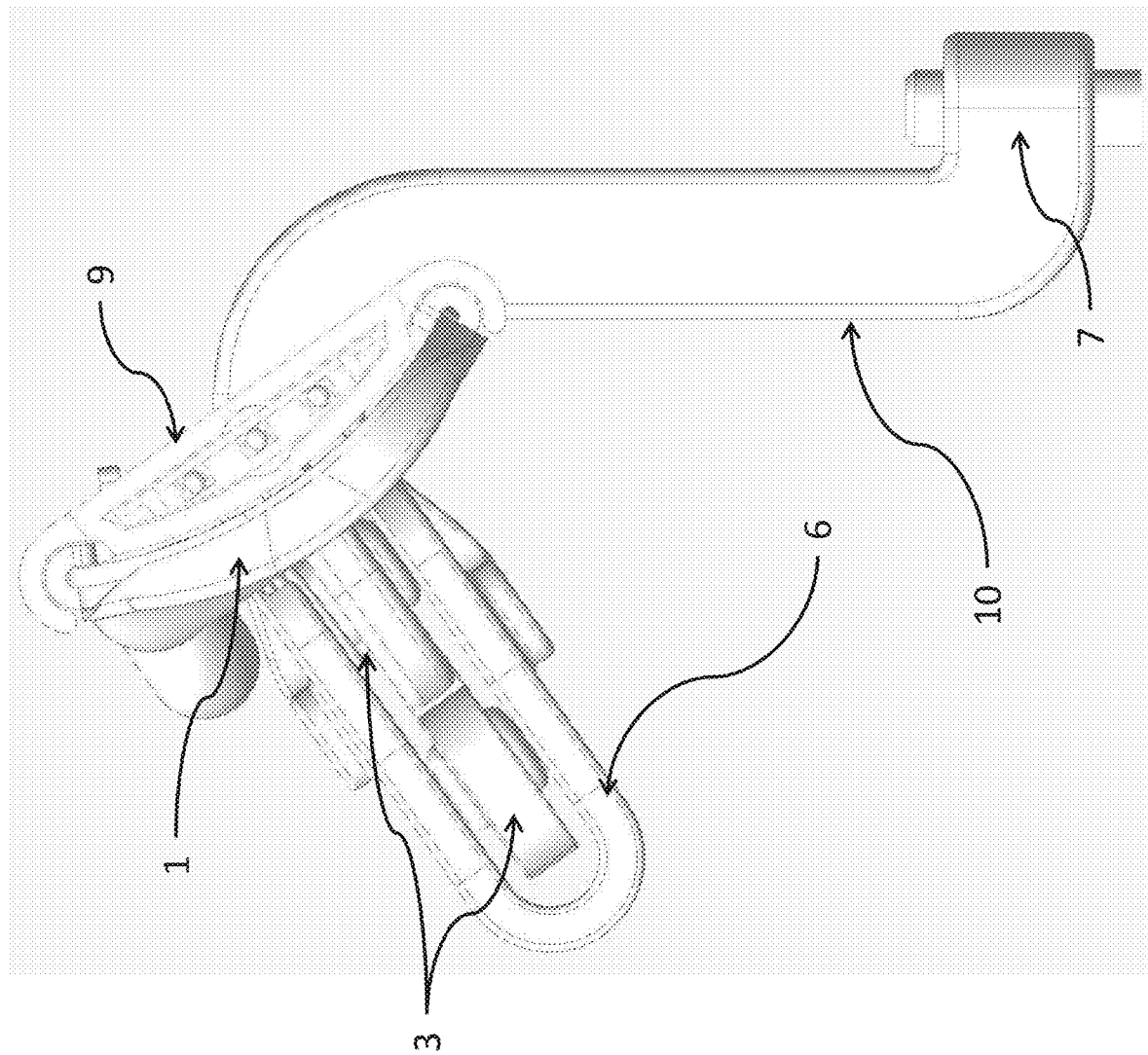
FIG. 15. Shows a close-up front view of another embodiment of an exemplary Universal Speculum wherein the blade is at the top most position on the column and the blade assembly is pivoted.
Figure 16:
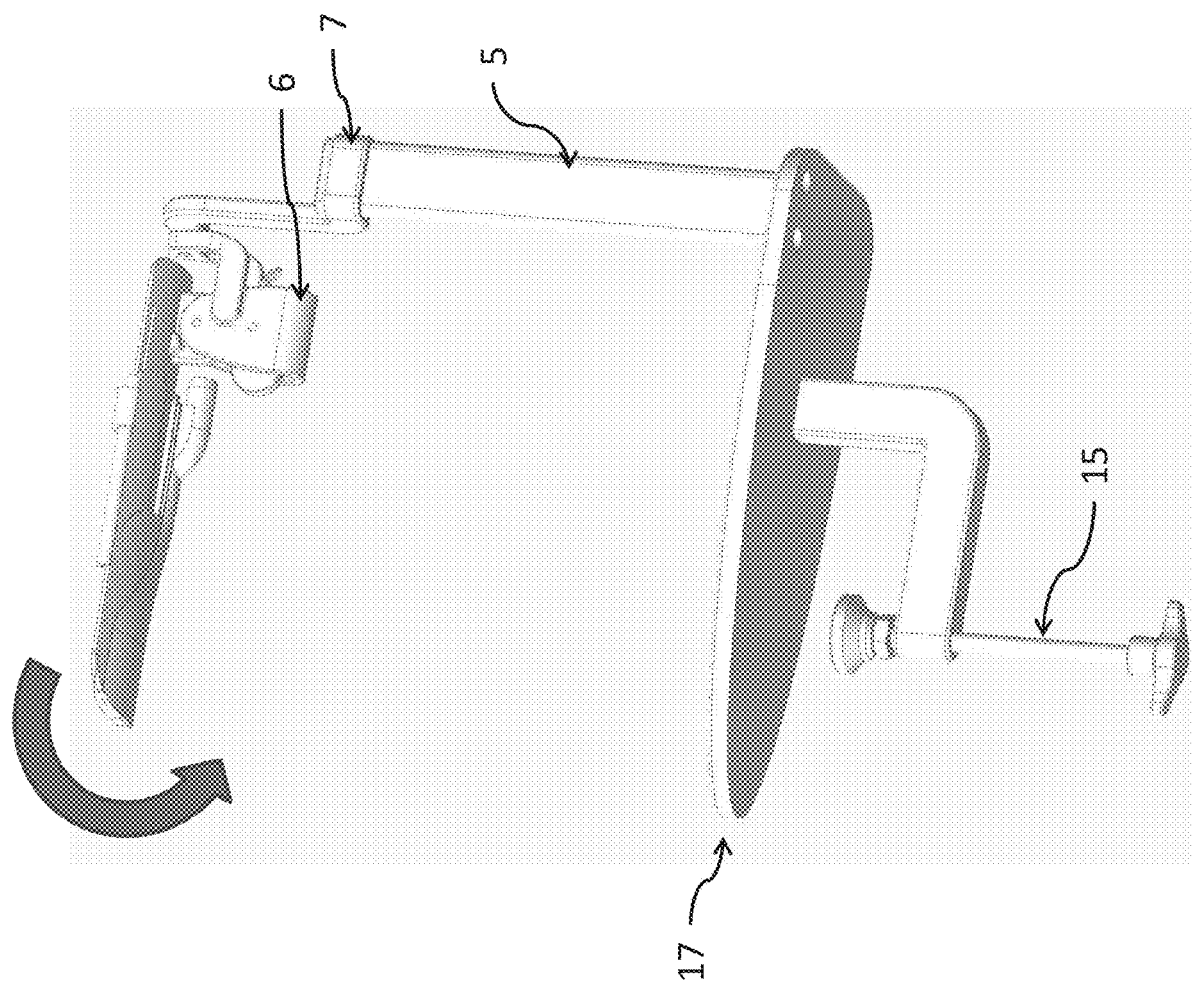
FIG. 16. Shows an isometric view of another embodiment of an exemplary Universal Speculum looking from the bottom up wherein the blade is extended and at the top most position on the column indicating the rotational angel of the blade motion.
Figure 17:
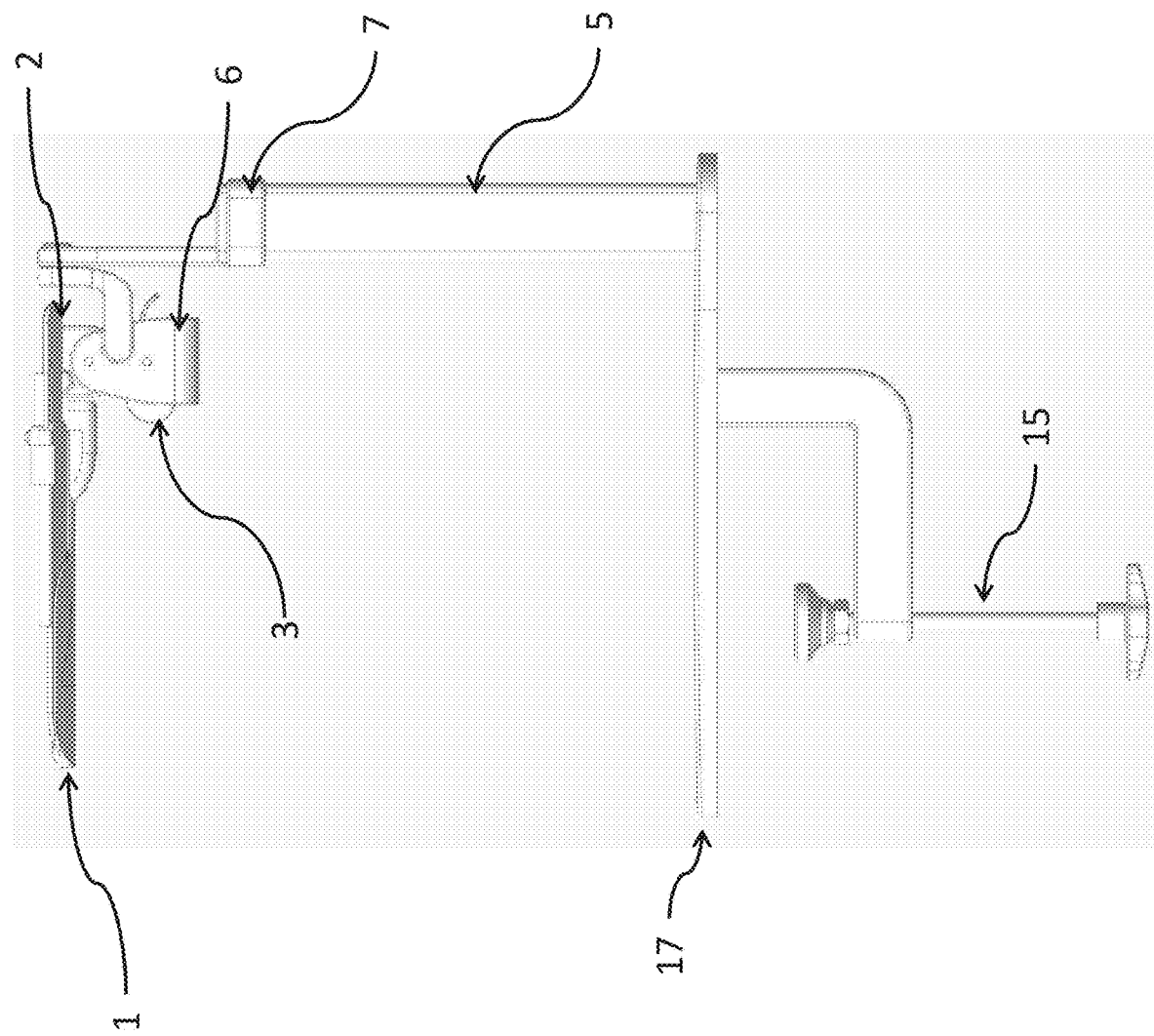
FIG. 17. Shows a side view of another embodiment of an exemplary Universal Speculum wherein the blade is extended and at the top most position on the column.
Figure 18:
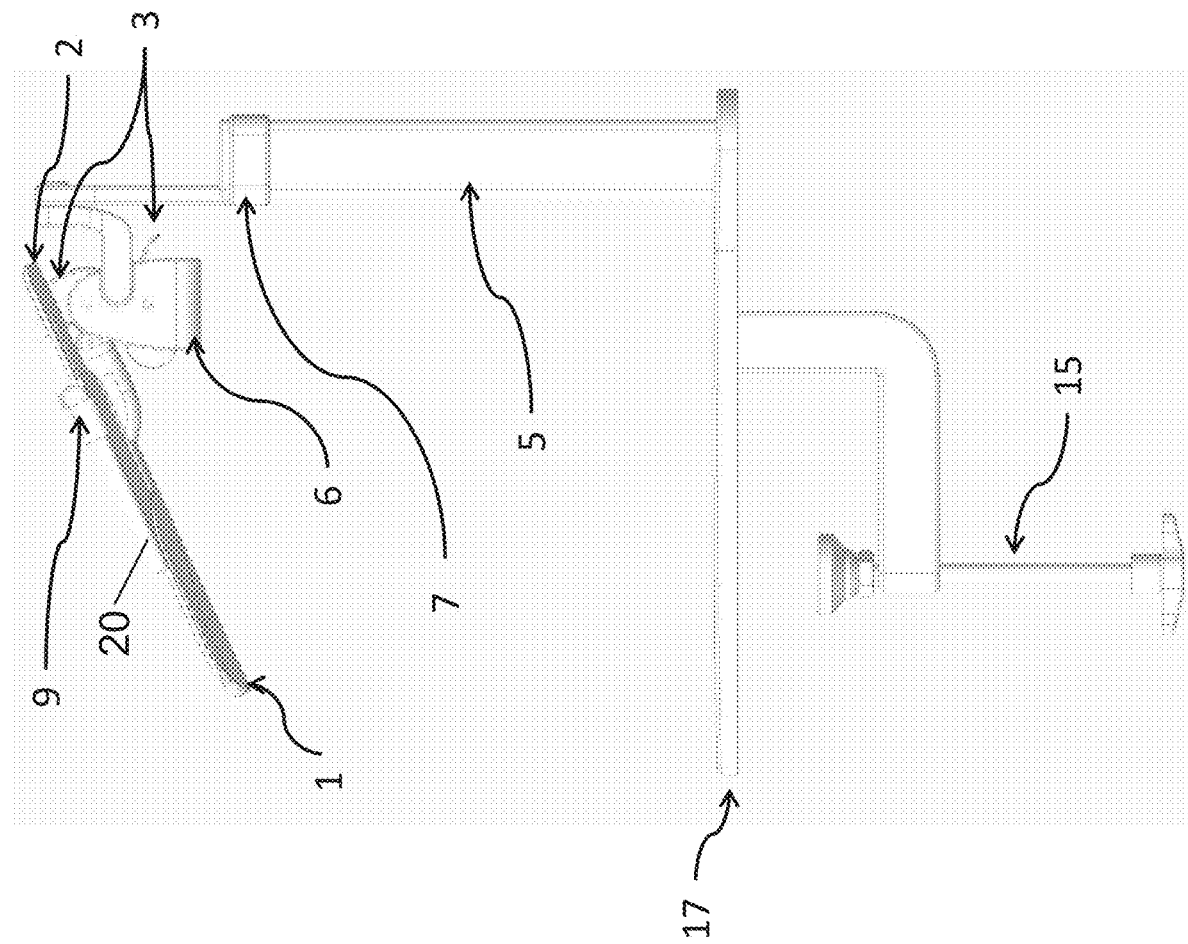
FIG. 18. Shows a side view of another embodiment of an exemplary Universal Speculum wherein the blade is extended, on an angle, and at the top most position on the column.
Figure 19:
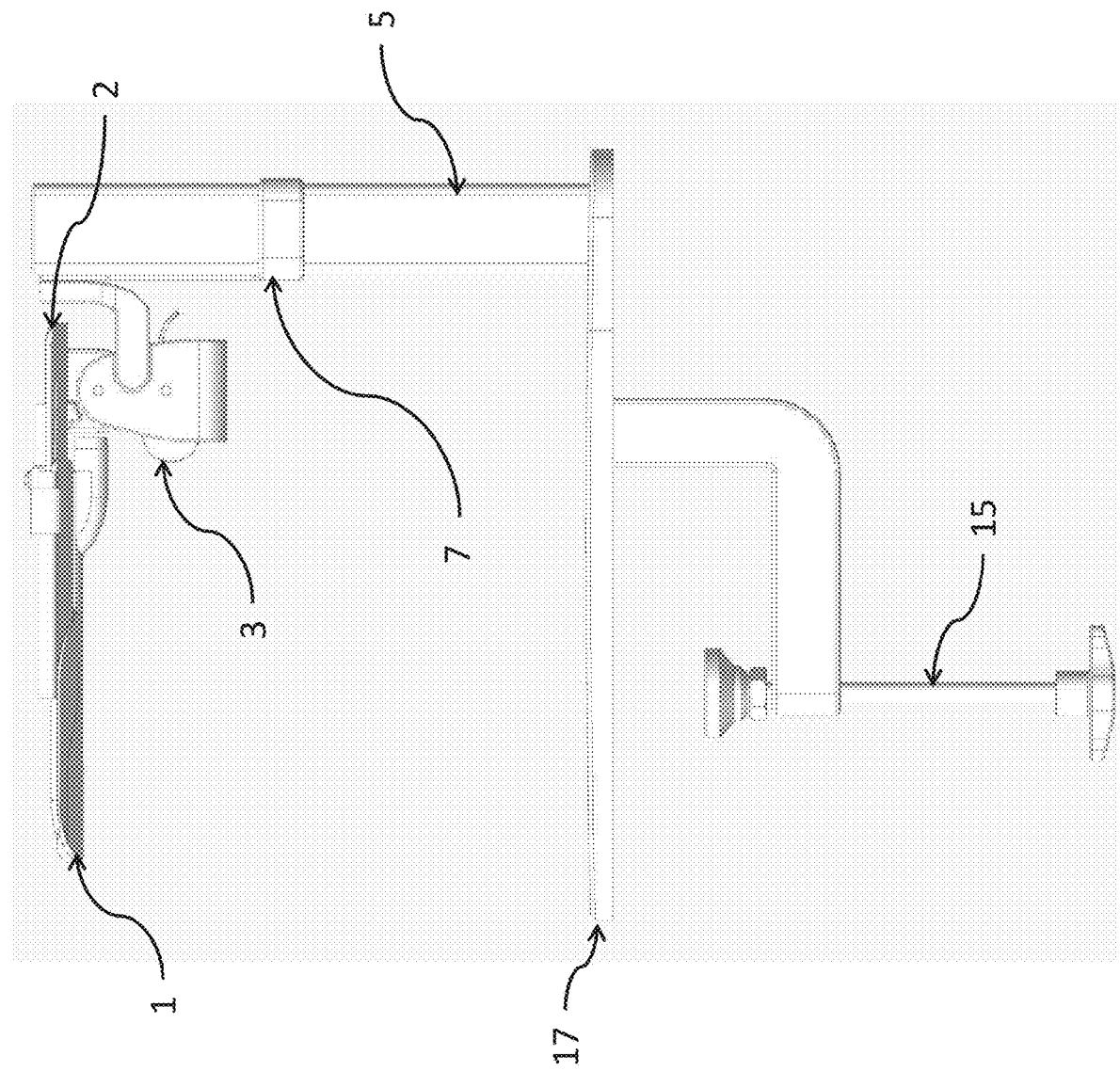
FIG. 19. Shows a side view of another embodiment of an exemplary Universal Speculum wherein the blade is extended and at the bottom most position on the column.
Figure 20:
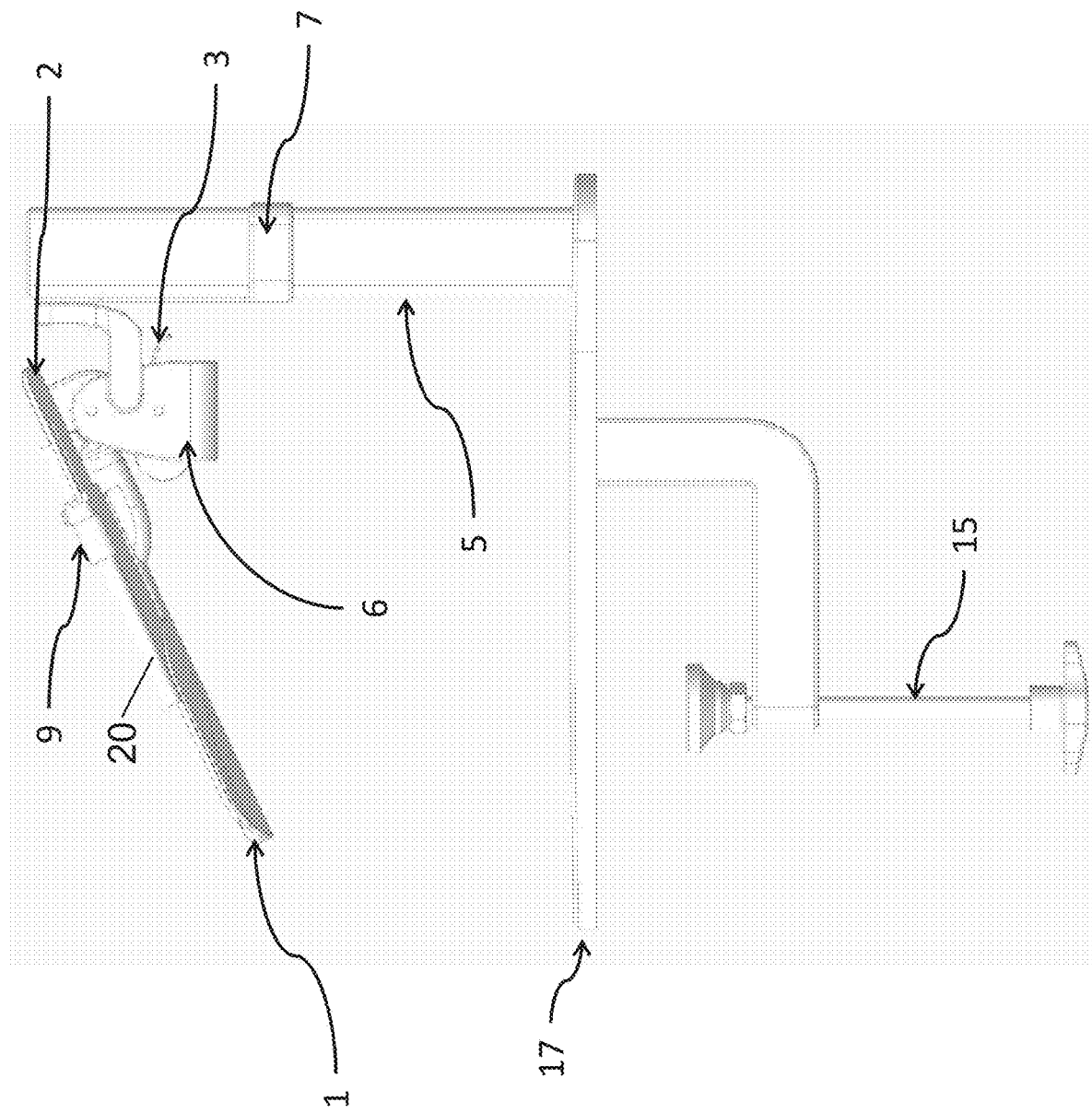
FIG. 20. Shows a side view of another embodiment of an exemplary Universal Speculum wherein the blade is retracted, on an angle, and at the bottom most position on the column.
Figure 21:
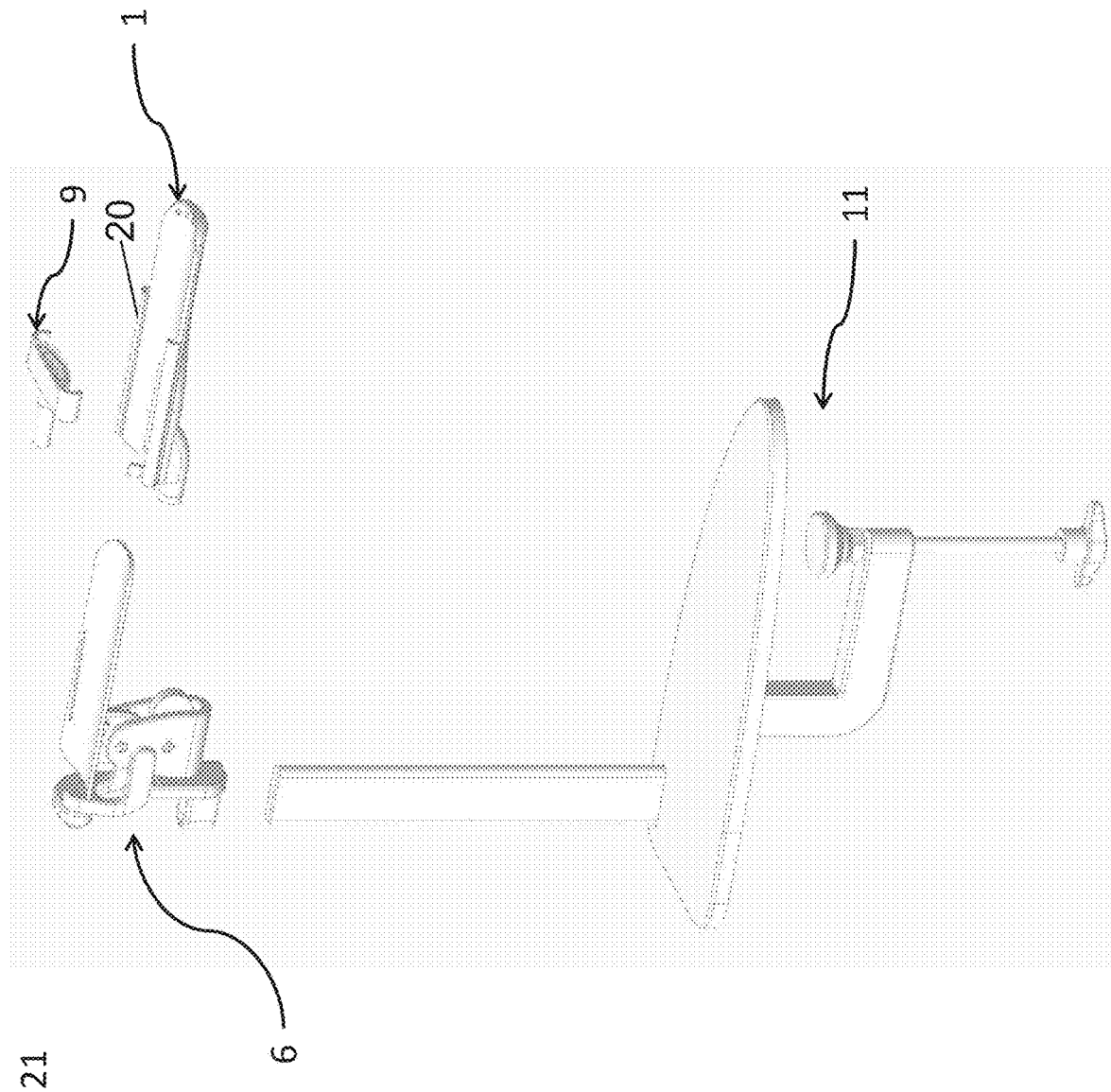
FIG. 21. Shows an exploded view of another embodiment of an exemplary Universal Speculum indicating the four main components.
Figure 22:
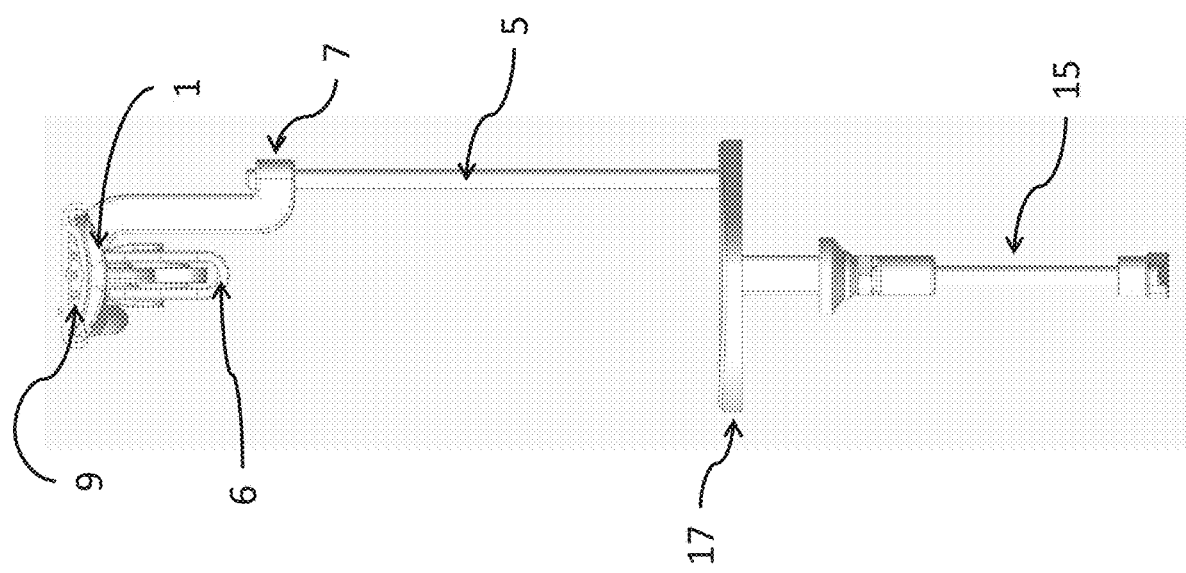
FIG. 22. Shows a front view of another embodiment an exemplary Universal Speculum herein the blade is at the top most position on the column.

FIG. 2 shows the blade assembly attached to the slider track (16) that topically allows rotation of the blade assembly of at least 15 degrees to the right of the midline and at least 15 degrees to the left of the midline for vertical position. FIG. 14 shows the blade assembly attached to a slider arm (10) via a pivoting connection (14) which allows for 360 degrees rotation of the blade assembly.

As shown on the drawings the blade assembly (4) is mounted on a support structure [6] with fasteners, which will allow the blade assembly (4) to travel up and down along one or more columns (5). It has a clamping base (11), which acts as the fulcrum, and at least one column (5) which allows for height adjustment of the blade assembly (4) from the surface of the surgical table to the posterior angle of the vaginal opening. The upper portion of the clamping base (11) is designed to slide between the top of the surgical table and the foam table pad, while the bottom screwing knob secures the base (17) to the table by clamping.

An additional, forward-facing, clip-on light assembly (9) can be added to improve visibility during operation. As shown in the drawings, the speculum may include rails (20), which are provided to allow an extension of the movable blade (1) beyond the length of the fixed blade (2).

The process/steps for use of the Universal Vaginal Speculum are as follows:

select a blade assembly comprising: a support structure and two blades wherein a first blade is a fixed blade and a second blade is a movable blade wherein the movable blade can extend beyond a length of the fixed blade; a blade angle mechanism as part of the blade assembly; a blade pivoting mechanism as part of the blade assembly; at least one column mounted on a base assembly; the blade assembly mounted on the at least one column on the base;

place the patient in the lithotomy position;

prep a patient and insert a pelvic drape between a pad and a hard surface of a table;

insert a base of the vaginal speculum between the pad and the hard surface of the table and secure the base to the table using a clamping mechanism;

extend the movable blade of the speculum to match a patient's depth of the vagina (blade assembly can be simultaneously inserted into the vagina);

adjust the height of the blade assembly such that the blades lie on the surface of the posterior wall of the vagina;

use the blade angle mechanism and the blade pivoting mechanism to achieved optimal exposure without undue pressure against the vaginal wall (once reaching the maximal achievable exposure without undue pressure on the posterior wall, the ratchet system will keep the blade in this fixed position);

Complete the draping

At the end of surgery, the following steps should be followed:

Adjust the blade angle mechanism and the blade pivoting mechanism as needed for removal of the vaginal, release the clamping mechanism, and remove the vaginal speculum.

The construction of the current Universal Vaginal Speculum is radically different in design from any other speculum on the market at this time. By re-designing the surgical vaginal speculum there is now no need to have a variety of speculums since the current speculum addresses all the deficiencies of the currently available speculums.

More specifically, it is self-retaining, adjusts for variable vaginal depths, adjusts to the variable posterior vaginal angle, and adjusts for increased access to the side walls, thus allowing for maximum exposure of the canal.

Figure 10:
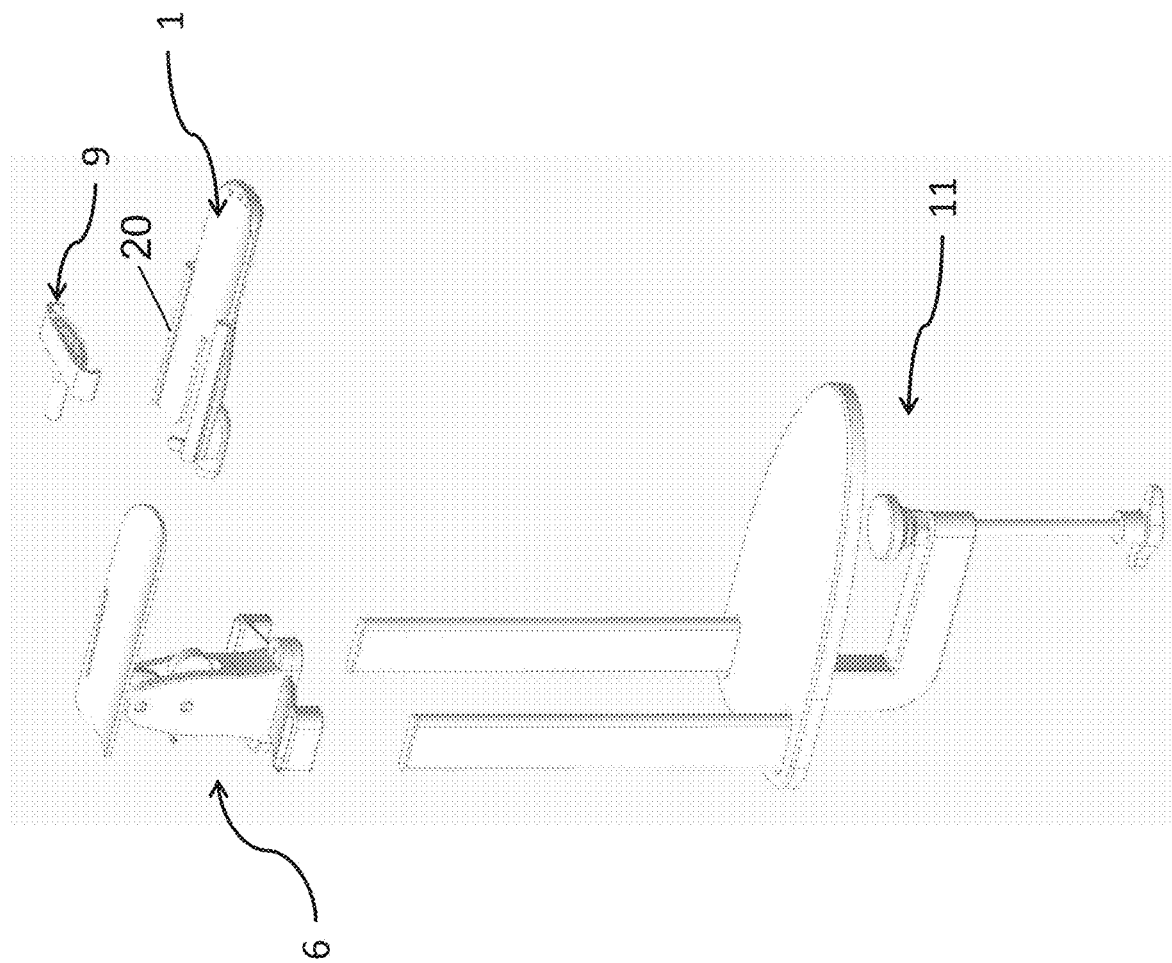
FIG. 10. Shows an exploded view of an exemplary Universal Speculum indicating the four main components.
Figure 11:
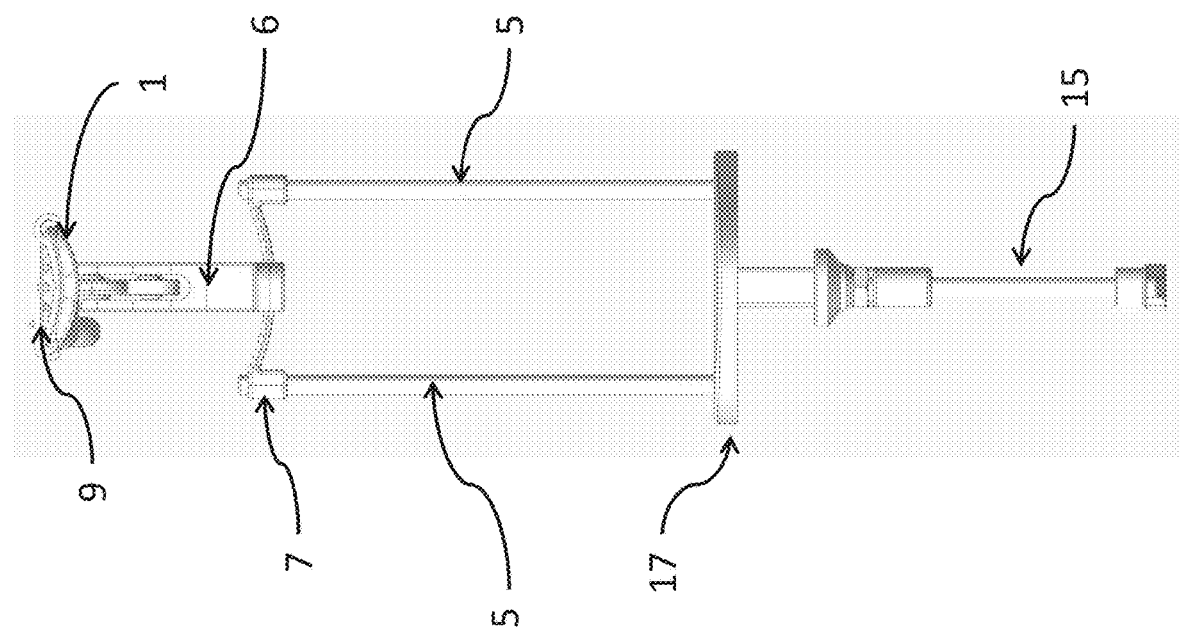
FIG. 11. Shows a front view of an exemplary Universal Speculum wherein the blade is at the top most position on the columns.
Figure 12:
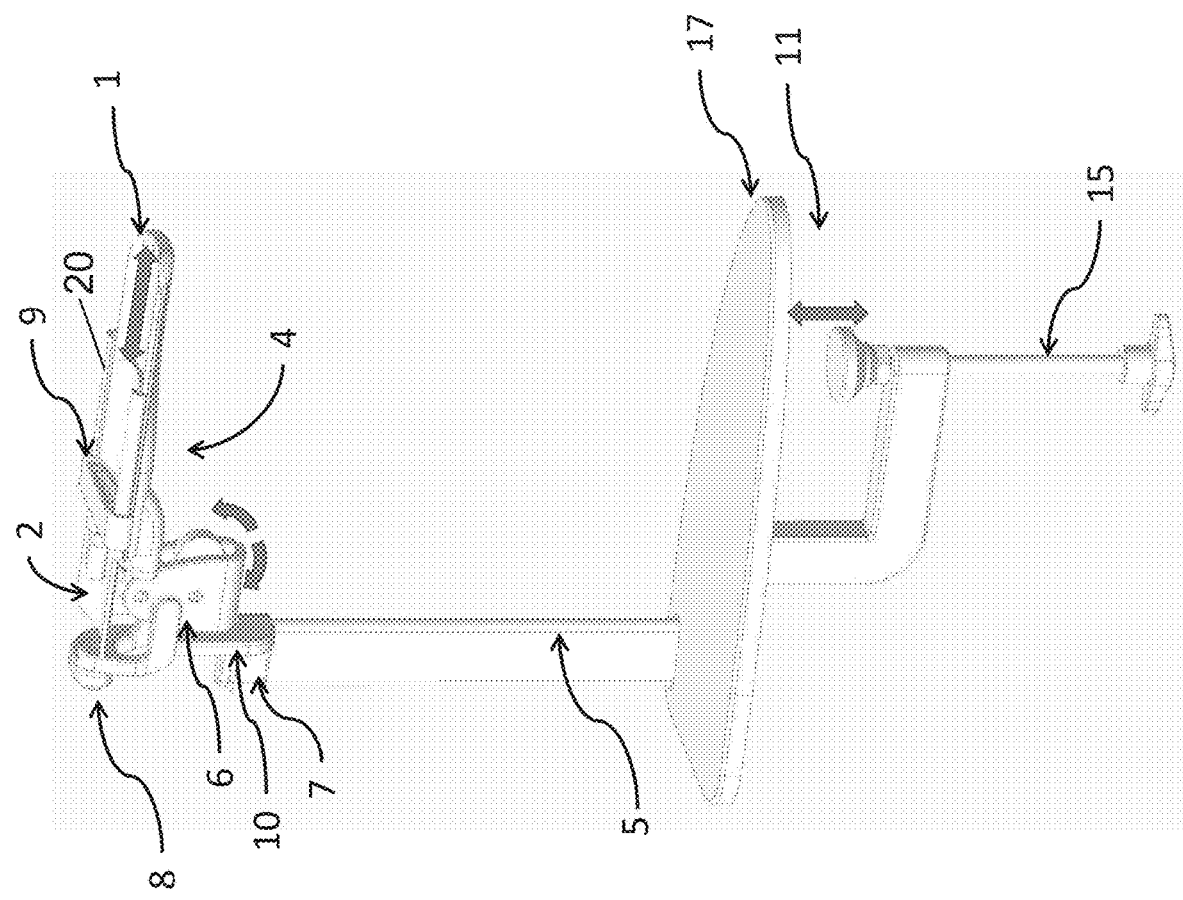
FIG. 12. Shows an isometric view of another embodiment of an exemplary Universal Speculum wherein the blade is extended and at the top most position on the column.
Figure 13:
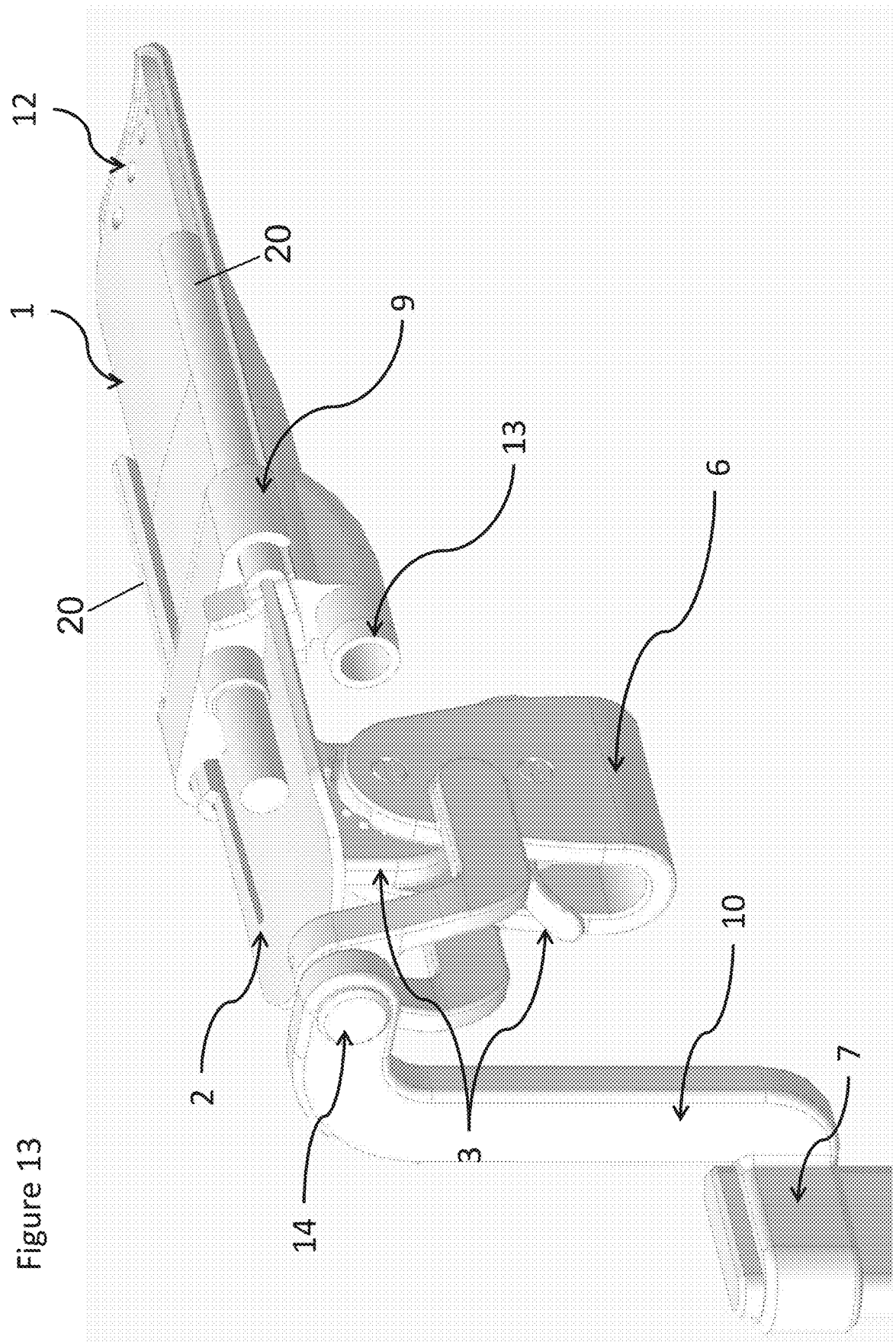
FIG. 13. Shows a close-up isometric view of another embodiment of an exemplary Universal Speculum wherein the blade is extended and the ratchet back side in view.

The new Universal Vaginal Speculum can be created in 4 components; blade assembly (4), extended blade (1), light (9), and clamping base assembly (11) which can be easily assembled and taken apart for proper sterilization (FIG. 10).

The above is a detailed description of particular embodiments of the invention. It is recognized that departures from the disclosed embodiments may be made within the scope of the invention and that obvious modifications will occur to a person skilled in the art. Those of skill in the art should, in light of the present disclosure, appreciate that many changes can be made in the specific embodiments which are disclosed herein and still obtain a like or similar result without departing from the spirit and scope of the invention. All of the embodiments disclosed and claimed herein can be made and executed without undue experimentation in light of the present disclosure.

What is claimed is:

1. A vaginal speculum comprising:
    a blade assembly comprising:
       a support structure;
       a fixed blade;
       a movable blade, wherein a distal edge of a longitudinal length of the movable blade is capable of extending beyond a distal edge of a longitudinal length of the fixed blade;
       a blade angle mechanism configured to rotate the fixed and moveable blades around a latitudinal axis of the fixed and moveable blades so as to control an angle of the fixed and movable blades with respect to the base; and
       a blade pivoting mechanism configured to rotate the fixed and moveable blades around a longitudinal axis of the fixed and moveable blades; and
    at least one column mounted on a base, wherein the blade assembly is mounted on the at least one column.

2. The vaginal speculum of claim 1, wherein the blade angle mechanism comprises a ratcheting mechanism mounted on the support structure and attached to the fixed blade.

3. The vaginal speculum of claim 1, wherein the blade pivoting mechanism comprises a pivot track on which the blade assembly is mounted.

4. The vaginal speculum of claim 1, wherein the support structure of the blade assembly is mounted on only one column extending from the base.

5. The vaginal speculum of claim 1, wherein the blade pivoting mechanism is a pivot connection on the blade assembly.

6. The vaginal speculum of claim 1, further comprising rails configured to allow the distal edge of the longitudinal length of the movable blade to extend beyond the distal edge of the longitudinal length of the fixed blade.

7. The vaginal speculum of claim 1, further comprising a light on the blade assembly.

8. The vaginal speculum of claim 1, wherein the movable blade includes an internal cavity and at least one vacuum opening near the distal edge of the movable blade.

9. The vaginal speculum of claim 1, wherein the support structure further comprises one or more slides for mounting the blade assembly on the at least one column.

10. A vaginal speculum comprising:
    a blade assembly comprising a support structure, a fixed blade, and a movable blade, wherein the movable blade is capable of extending beyond a length of the fixed blade;
    a blade pivoting mechanism; and
    two columns in parallel to each other and extending from a base, wherein the support structure of the blade assembly is mounted on the two columns.

11. The vaginal speculum of claim 10, wherein the blade assembly further comprises a blade angle mechanism configured to rotate the fixed and moveable blades around a latitudinal axis of the fixed and moveable blades so as to control an angle of the fixed blade and movable blades with respect to the base, and the blade pivoting mechanism is configured to rotate the fixed and moveable blades around a longitudinal axis of the fixed and moveable blades.

12. The vaginal speculum of claim 10, further comprising rails configured to allow the movable blade to extend beyond the length of the fixed blade.

13. The vaginal speculum of claim 10, wherein the support structure further comprises one or more slides for mounting the blade assembly on the at least one column.

14. A vaginal speculum comprising:
    a blade assembly comprising a support structure, a first blade, and a second blade;
    at least one column mounted on a base, wherein the blade assembly is mounted on the at least one column;
    a blade angle mechanism configured to rotate the first and second blades around a latitudinal axis of the first and second blades so as to control an angle of the first and second blades with respect to the base; and
    a blade pivoting mechanism configured to rotate the first and second blades around a longitudinal axis of the first and second blades.

15. The vaginal speculum of claim 14, wherein the blade angle mechanism comprises a ratcheting mechanism mounted on the support structure and attached to the first blade.

16. The vaginal speculum of claim 14, wherein at least one of the first and second blades includes an internal cavity and at least one vacuum opening near a distal edge of the at least one of the first and second blades.

17. The vaginal speculum of claim 14, wherein the blade pivoting mechanism comprises a pivot track on which the blade assembly is mounted.

18. The vaginal speculum of claim 14, wherein the support structure of the blade assembly is mounted on only one column extending from the base.

19. The vaginal speculum of claim 14, wherein the blade pivoting mechanism is a pivot connection on the blade assembly.

20. The vaginal speculum of claim 14, further comprising a light on the blade assembly.

21. The vaginal speculum of claim 14, wherein the support structure further comprises one or more slides for mounting the blade assembly on the at least one column.

22. The vaginal speculum of claim 14, further comprising rails configured to allow the movable blade to extend beyond a length of the fixed blade.

* * * * *